US006344184B1

(12) United States Patent
Rolla

(10) Patent No.: US 6,344,184 B1
(45) Date of Patent: Feb. 5, 2002

(54) ORAL COMPOSITION FOR INHIBITING ORAL MALODOR

(75) Inventor: Gunnar Rolla, Oslo (NO)

(73) Assignee: Orix AS, Bekkestua (NO)

( * ) Notice: Subject to any disclaimer, the term of this patent is extended or adjusted under 35 U.S.C. 154(b) by 0 days.

(21) Appl. No.: 09/615,944

(22) Filed: Jul. 13, 2000

Related U.S. Application Data

(63) Continuation of application No. PCT/NO99/00346, filed on Nov. 16, 1999.

(30) Foreign Application Priority Data

Mar. 1, 1999 (NO) .......................... 1999 0975

(51) Int. Cl.⁷ .......................... A61K 7/16; A61K 7/22; A61K 33/30
(52) U.S. Cl. .......................... 424/54; 424/49
(58) Field of Search .............. 424/49–58, 641, 424/642, 643

(56) References Cited

U.S. PATENT DOCUMENTS

| 4,522,806 A |   | 6/1985  | Muhlemann et al. | 424/52 |
|-------------|---|---------|------------------|--------|
| 4,568,540 A | * | 2/1986  | Asanlo et al.    | 424/52 |
| 4,689,214 A | * | 8/1987  | Niles et al.     | 424/49 |
| 4,992,259 A | * | 2/1991  | Schiraldt et al. | 424/49 |
| 5,286,479 A | * | 2/1994  | Garlich et al.   | 424/54 |
| 5,405,836 A | * | 4/1995  | Richar et al.    | 424/49 |
| 5,753,217 A | * | 5/1998  | Christopfel      | 424/53 |
| 5,827,503 A | * | 10/1998 | Schwabe          | 424/54 |
| 5,833,952 A | * | 11/1998 | Grigor et al.    | 424/49 |
| 5,906,811 A |   | 5/1999  | Hersh            | 424/54 |
| 5,948,390 A |   | 9/1999  | Nelson et al.    | 424/54 |
| 6,030,605 A | * | 2/2000  | D'Amelia et al.  | 424/48 |
| 6,121,315 A | * | 9/2000  | Nair et al.      | 424/49 |

FOREIGN PATENT DOCUMENTS

| DE | 3001575   | 7/1981  |
| EP | 0 181 161 | 5/1985  |
| EP | 0 920 857 | 6/1999  |
| WO | 90/15592  | 12/1990 |

OTHER PUBLICATIONS

E. Giertsen et al., "Combined effects of $Zn^{2+}$–chlorhexidine and $Zn^{2+}$–cetylpyridinium chloride on caries incidence in partially desalivated rats", Scandinavian Journal of Dental Research, vol. 99, No. 4, (1991).

E. Giertsen et al., "In vivo Effects of Zinc and Chlorhexidine on Dental Plaque Ureolyis and Glycolysis", J. Dent. Res., vol. 68, No. 6, (Jun. 1989).

* cited by examiner

Primary Examiner—Shep K. Rose
(74) Attorney, Agent, or Firm—Wenderoth, Lind & Ponack, L.L.P.

(57) ABSTRACT

Oral composition for inhibiting oral malodor, containing an antibacterial agent and a zinc compound, in the form of a mouthwash containing 0.005–0.05% w/v of an antibacterial agent selected from bis-guanides and quaternary ammonium compounds, and 0.05–0.5% w/v of zinc acetate.

6 Claims, 20 Drawing Sheets

Figure 1:
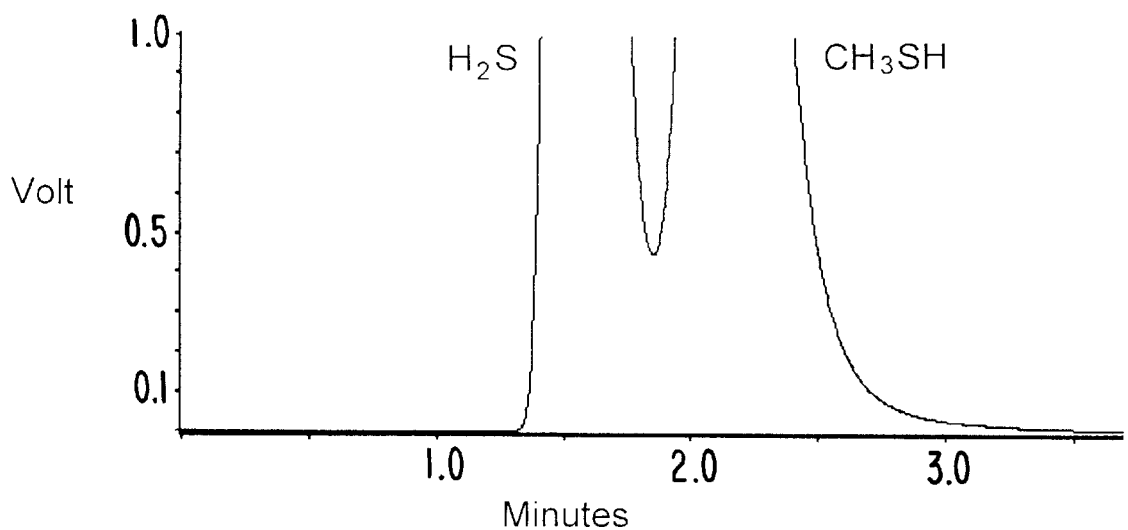

Sample ID: control
Acquired: Nov 20, 1998, 13:58:24

Results:

| Peak | Area |
|---|---|
| $H_2S$ | 28302550 |
| $CH_3SH$ | 41918978 |

Sample ID: saliva + 0,3% Zn acetate
Acquired: Nov 20, 1998, 14:12:06

Results:

| Peak | Area |
|---|---|
| $H_2S$ | 150256 |
| $CH_3SH$ | 4028796 |

Sample ID: saliva + 0,025% CHX
Acquired: Nov 20, 1998, 14:21:00

Results:

| Peak | Area |
|---|---|
| $H_2S$ | 443348 |
| $CH_3SH$ | 355001 |

Sample ID: saliva + 0,025% CPC
Acquired: Nov 20, 1998, 14:39:18

Results:

| Peak | Area |
|---|---|
| $H_2S$ | 5264229 |
| $CH_3SH$ | 6889886 |

Sample ID: saliva + 0,025% Banzlakonim Cl
Acquired: Nov 20, 1998, 14:29:40

Results:

| Peak | Area |
|---|---|
| $H_2S$ | 1402428 |
| $CH_3SH$ | 1757520 |

Sample ID: saliva + 0,3% Zn-ac./ 0,025% CHX
Acquired: Nov 20, 1998, 15:02:53

Results:

| Peak | Area |
|---|---|
| $H_2S$ | 82516 |
| $CH_3SH$ | 34430 |

Sample ID: saliva + 0,3% Zn-ac./ 0,025% Benzalkonium Cl
Acquired: Nov 20, 1998, 15:12:31

Results:

| Peak | Area |
|---|---|
| $H_2S$ | 46971 |
| $CH_3SH$ | 4063 |

Sample ID: saliva + 0,3% Zn-ac./ 0,025% CPC
Acquired: Nov 20, 1998, 15:17:18

Results:

| Peak | Area |
|---|---|
| $H_2S$ | 42749 |
| $CH_3SH$ | 12245 |

Sample ID: cysteine
Acquired: Jan 18, 1999, 09:59:59

Results:

| Peak | Area |
|---|---|
| H$_2$S | 10777763 |

Sample ID: cysteine 1h. after CHX / Zn
Acquired: Jan 18, 1999, 11:05:56

Results:

| Peak | Area |
|---|---|
| H₂S | 32230 |

Sample ID: cysteine 3h. after CHX / Zn
Acquired: Jan 18, 1999, 13:01:44

Results:

| Peak | Area |
|---|---|
| $H_2S$ | 277783 |

Sample ID: cysteine 4h. after CHX / Zn
Acquired:   Jan 18, 1999, 14:05:12

Results:

| Peak | Area |
|---|---|
| $H_2S$ | 1713244 |

Sample ID: cysteine 5h. after CHX / Zn
Acquired: Jan 18, 1999, 14:50:51

Results:

| Peak | Area |
| --- | --- |
| $H_2S$ | 1769030 |

Sample ID: cysteine
Acquired: Jan 19, 1999, 09:52:10

Results:

| Peak | Area |
|---|---|
| H$_2$S | 11646370 |

Sample ID: cysteine 1h. after CPC / Zn
Acquired: Jan 19, 1999, 11:04:09

Results:

| Peak | Area |
|------|------|
| H₂S  | 22209 |

Sample ID: cysteine 2h. after CPC / Zn
Acquired: Jan 19, 1999, 12:01:07

Results:

| Peak | Area |
|---|---|
| $H_2S$ | 67676 |

Sample ID: cysteine 3h. after CPC / Zn
Acquired: Jan 19, 1999, 12:56:33

Results:

| Peak | Area |
|---|---|
| $H_2S$ | 215678 |

Sample ID: cysteine 4h. after CPC / Zn
Acquired: Jan 19, 1999, 13:55:40

Results:

| Peak | Area |
|---|---|
| $H_2S$ | 275812 |

Sample ID: cysteine 5h. after CPC / Zn
Acquired: Jan 19, 1999, 15:12:20

Results:

| Peak | Area |
|---|---|
| $H_2S$ | 47342 |

ORAL COMPOSITION FOR INHIBITING ORAL MALODOR

This is a continuation of PCT application no. PCT/NO99/00346 filed Nov. 16, 1999.

The present invention relates to an oral composition which is effective against halitosis (oral malodor, foetor ex ore). Said composition is effective by eliminating or reducing the production of volatile sulfur compounds (VSCs) in the oral cavity. It is well established that in the majority of cases of halitosis this originates from the oral cavity and not from the stomach, as frequently believed by the public.

Bacteria located in the crypts at the back of the tongue and in periodontal pockets produce VSCs, mainly hydrogen sulfide (HS) and methyl mercaptan (MM). The bacteria produce these by proteolytic, anaerobic metabolism, and they have an extremely unpleasant odor even in very low concentrations. The VSCs are able to penetrate epithelium and have pathogenic potentials by damaging cells of the underlying tissues and also affect their metabolism. It has been suggested that the VSCs produced by bacteria in periodontal pockets may well be an important factor in the development of periodontal disease. MM appears to have a higher pathogenic potential than HS and has also a more offensive odor.

The most important substrate for HS production in the oral cavity appears to be cysteine. HS forms immediately upon rinsing the mouth with an aqueous solution of this amino acid (see example 2). Methionine is a major substrate for MM formation, although this compound is not as rapidly formed in the oral cavity as hydrogen sulfide.

It Is known that zinc ions reduce the VSC production in the oral cavity. The mechanism involved presumably involves a reaction between zinc and sulfur whereby nonvolatile sulfides are formed and thus inhibit the transformation of sulfur containing substrates to VSCs. Zinc furthermore possesses a certain antibacterial activity and this metal ion is known to be able to inhibit plaque formation and reduce acid formation in dental plaque. The zinc salts usually used for such purposes are the chloride, the sulfate and the citrate. However, aqueous solutions of the two former salts have low pH and are thus not necessarily suited for oral use whereas solutions of zinc citrate contain complexes of zinc and citrate and very few free zinc ions.

The problem of getting zinc in a suitable form is the issue of U.S. Pat. No. 4,289,753 and UK Patent Application No. 2,052,978. In the former the zinc compound used is an ammonium or alkali metal citrate. It is also stated In this patent that this zinc compound may be used in combination with antibacterial agents such as cetyl pyridinium chloride.

The above UK Patent Application discloses an oral composition in which the pH of a zinc containing solution is adjusted to 4.5 or 8 by means of glycine. The zinc is generally present as zinc chloride.

Antibacterial agents such as cationic bis-biguanides and quaternary ammonium compounds, have been widely used in preventive dentistry as inhibitors of plaque formation and of development of gingivitis. The bis-biguanide chlorhexidine is frequently used for this purpose, usually as an aqueous solution of 0.2% of its gluconate salt, and is applied as a mouthrinse twice daily. Such concentration and frequency are necessary to obtain consistent clinical plaque inhibition. However, chlorhexidine in these concentrations has a bitter taste and causes dental stain. Chlorhexidine forms salts of low solubility with chloride, sulfate and citrate and is thus not compatible with zinc containing these anions.

The other cationic antibacterial agents which inhibit plaque formation, for example cetylpyridinium chloride or benzalkonium chloride, have less clinical effect, but show a less pronounced tendency to cause dental stain. The cationic antibacterial agents mentioned above are able to inhibit VSC formation in the oral cavity, but relatively high concentrations are needed (see Example 1).

Figure 2:
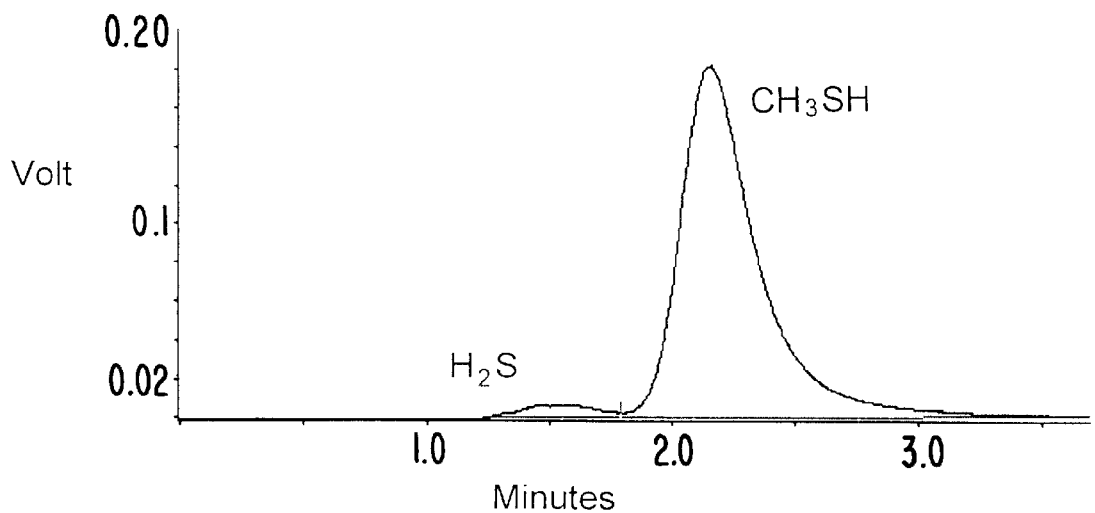
Figure 3:
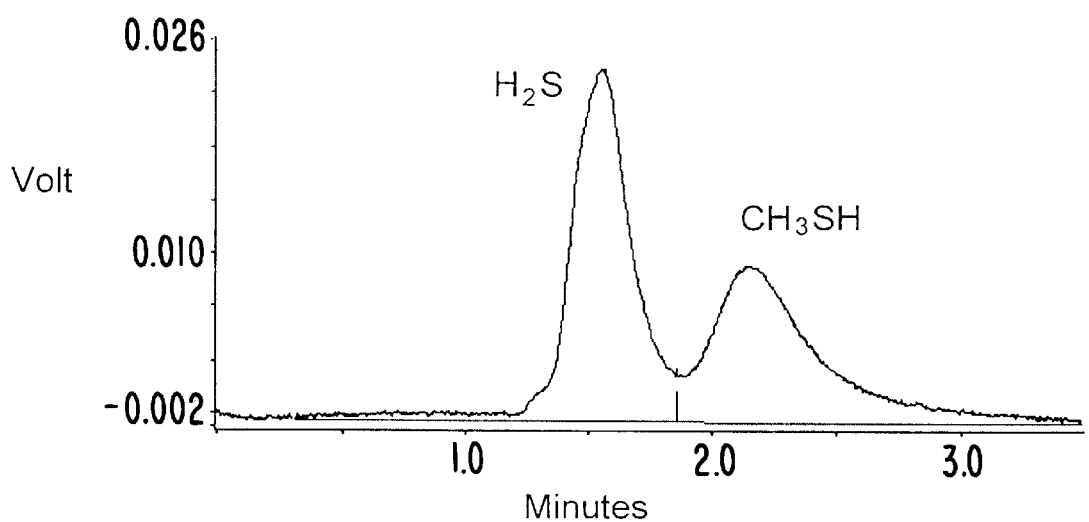
Figure 4:
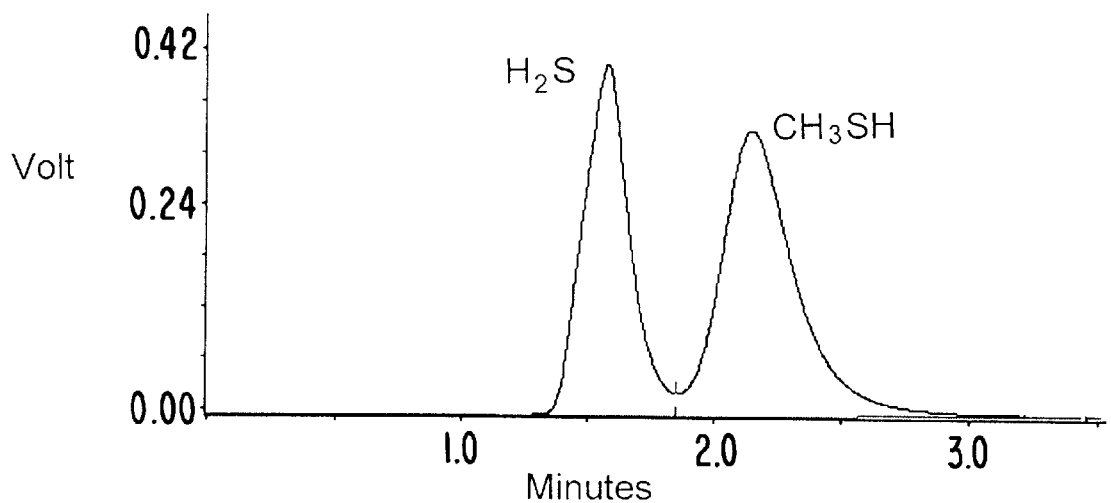
Figure 5:
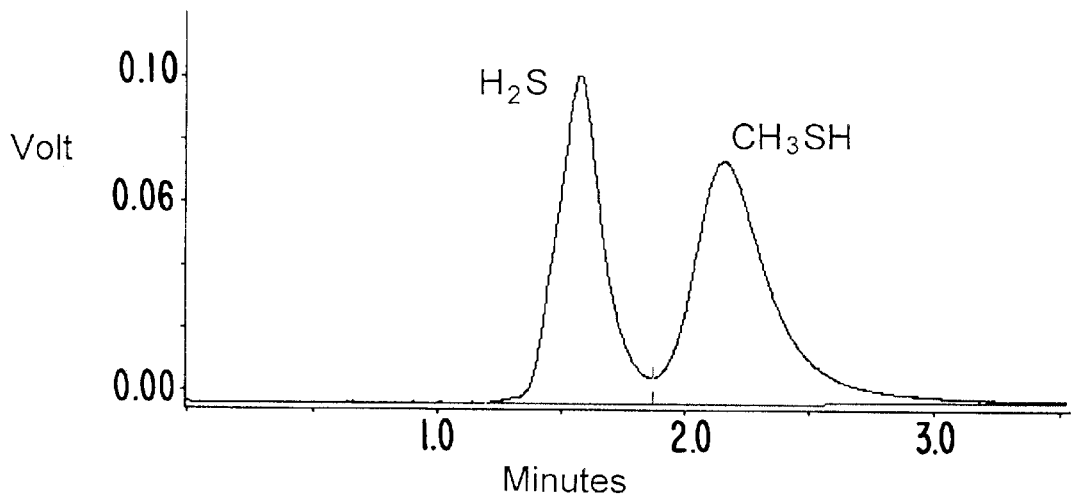
Figure 6:
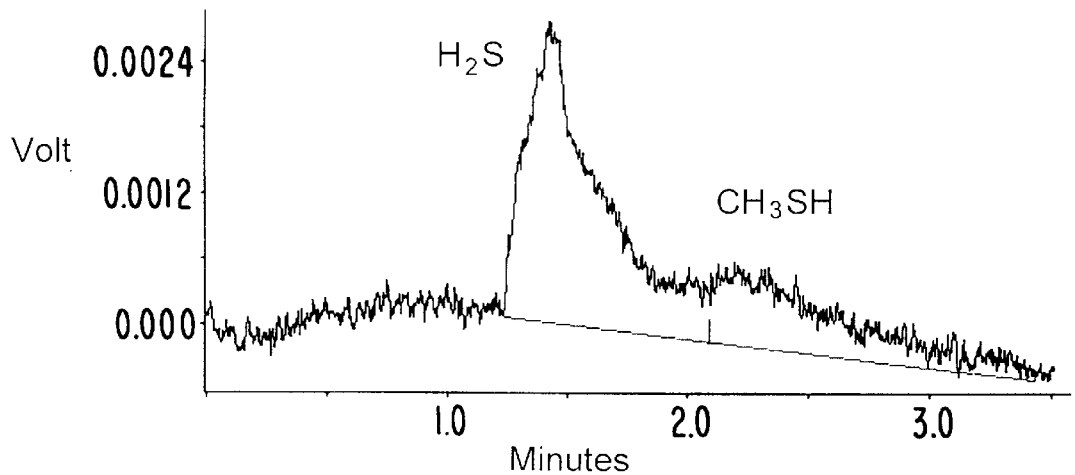
Figure 7:
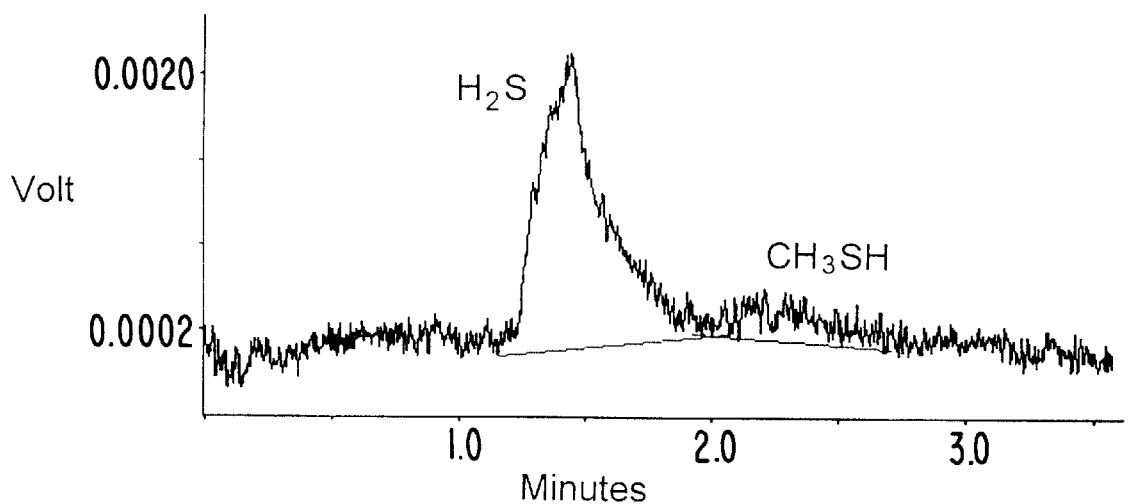
Figure 8:
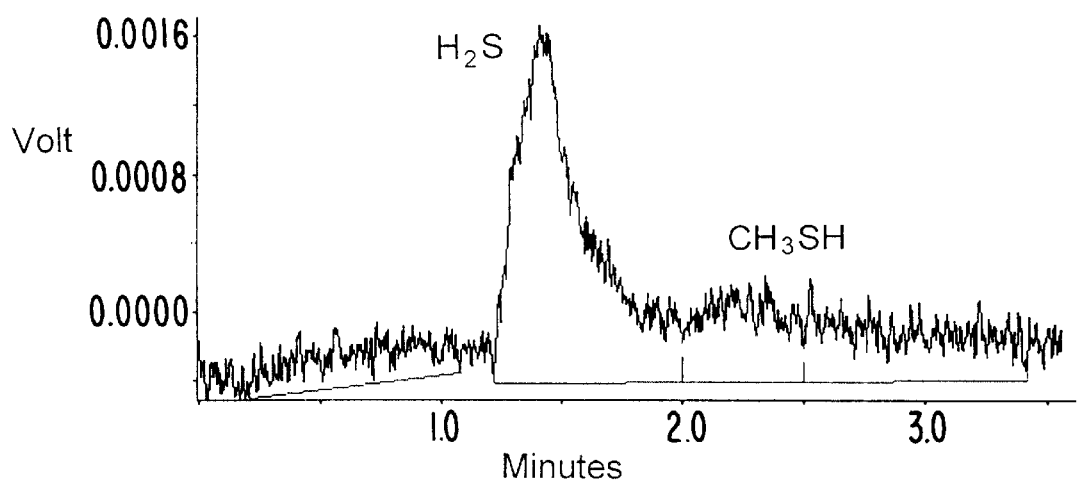

It has now unexpectedly been found that anti-VSC effect of zinc Ions Is mainly directed against hydrogen sulfide production and to a far lesser extent against the production of methyl mercaptan (see Example 1, FIG. 2). The VSC species with highest pathogenic potential and the most unpleasant odor i.e. MM, is thus incompletely eliminated by zinc ions.

This selective effect on HS by zinc can presumably be explained by the fact that cysteine (which is major substrate for HS formation) has an exposed —SH group, which will react readily with zinc ions, whereas methionine (which is a substrate for MM formation) has no such group. When hydrogen sulfide Is dissolved in water (or saliva) HS— and S— are formed (together with two protons), and both these sulfur containing intermediates react rapidly with zinc ions to form insoluble sulfides.

It was furthermore unexpectedly found that when a combination of zinc ions and very low concentrations of certain cationic antibacterial agents were used, the combinations inhibited both HS and MM formation. The effect of the combinations is synergistic (Example 1, table 1) The combinations of zinc and low concentrations of antibacterial agent caused a much higher inhibition of VSCs than any of the individual agents alone. The concentration of an antibacterial agent used in this way against oral malodor was markedly lower than the concentrations needed to obtain plaque inhibition or reduced acid formation in plaque (¹/₁₀ or less).

The importance of this invention resides in the fact that It allows the use of very low concentrations of antibacterial agents, i.e. concentrations where their undesired side effects are avoided. The contribution of the antibacterial agent is probably mainly to inhibit MM formation, but synergistic effect with zinc against HS was also observed, although not to the same degree as against MM. The concentration of zinc can also be kept lower than when zinc is used alone, for the same reason. Zinc has a metallic taste which is concentration dependent.

The use of combinations of zinc acetate and chlorhexidine is described in DE 30001575 A1. However, the purpose is to avoid discoloration of teeth by chlorhexidine. In U.S. Pat. No. 4,522,806 an anti-plaque effect of the combination of chlorhexidine and zinc acetate is mentioned (page 5, first paragraph). The combination was found to be numerically better than chlorhexidine alone, but the difference was not statistically significant.

In U.S. Pat. No. 5,906,811 a combination of zinc acetate and benzalkoniumchloride is mentioned as an ingredient in tooth-pastes. The main purpose is to avoid damage from free radical species on the oropharyngeal cavity of tobacco smokers, including secondary smokers.

The present invention provides an oral composition for inhibiting oral malodor, comprising an antibacterial agent and a zinc compound. The composition is in the form of a mouthwash containing 0.005–0.05% wt of an antibacterial agent selected from bis-biguanides and quaternary ammonium compounds, and 0.05–0.5% w/v zinc acetate.

When zinc acetate is used together with an antibacterial agent selected from the bis-biguanides or quaternary ammonium compounds, the effect appears to be synergistic, as mentioned above. This means that by using such a combination, the amount of both (i.e. zinc acetate and anti-bacterial agent) may be kept very low. By using such low amounts the bitterness of the taste and the tendency to cause dental stain will both be avoided.

A major benefit of this invention is that it allows the use of much lower concentrations of antibacterials In compositions specially designed to inhibit oral malodor, than in ordinary products intended for anti-plaque and anti-gingivitis purposes.

The low concentrations of the antibacterial agent is favorable both from an economical and toxicological point of view. The presence of zinc in itself reduces the tendency to cause dental stain, because zinc sulfide is white or gray, whereas the other metal sulfides which form on teeth are black, brown or yellow.

As mentioned above it is a great advantage that the concentrations of the two ingredients, in particular the concentration of the antibacterial agent, can be kept very low, This is particularly easy to control in a mouthrinse where the concentrations of said active ingredients can be readily adjusted to the desired value. According to a particularly preferred embodiment the oral composition of the invention is in the form of a mouthrinse containing from 0.01% to 0.025% w/v of the antibacterials and 0.1% to 0.3% w/v of zinc acetate.

As mentioned above, a preferred antibacterial agent is chlorhexidine or a salt thereof, in particular the acetate or the gluconate salts. Preferred quaternary ammonium compounds are cetyl pyridinium chloride or benzalkonium chloride.

According to another embodiment of the invention a composition comprising an antibacterial agent selected from the bis-biguanides and the quaternary ammonium compounds, and zinc acetate, is used for the preparation of an oral composition in particular in a mouthrinse, for inhibiting oral malodor.

In a further embodiment of the invention a composition containing an antibacterial agent selected from bis-biguanides an quaternary ammonium compounds, and zinc acetate, is used for the treatment of oral malodor. In the use indicated above, the amounts of the components should be as described above in connection with the oral composition.

EXAMPLE 1

In vitro experiments were performed to test the VSC-inhibiting potential of different combinations of zinc acetate and cationic antibacterial agents.

To a 1 ml sample of freshly collected human saliva in a test tube was added 10 microliter of the solutions (mouthrinses) described below. The test tubes were closed with a stopper and incubated overnight at 37° C. A control tube which contained only saliva served as a control. It is well known that large amounts of VSCs are formed in a test tube during the latter conditions, the bacteria breaking down the salivary proteins and forming VSCs from cysteine and methionine. The VSCs in the gas phase above the incubated saliva, were measured by gas chromatography in a Shimadzu 14B instrument, and hydrogen sulfide, methyl mercaptan and di-methyl sulfide were used as standard.

The solutions to be tested were: 0.3% zinc acetate, 0.025% chlorhexidine, 0.025% cetylpyridinium chloride and 0.025% benzalkonium chlorides. Subsequently the zinc acetate was combined with each of the individual antibacterial agents. All the experiments described In this paragraph were performed on the same day under Identical conditions. The concentrations chosen were based on experience from pilot experiments with different concentrations of the zinc and antibacterial agents. The results can be seen from the chromatograms in FIGS. 1–8, and from table 1 below.

The experiments showed that the control contained very high amounts of both hydrogen sulfide (HS) and methyl mercaptan (MM), whereas the samples which contained zinc had low amounts of both HS and MM. It was, however, found that the zinc acetate reduced the amount of HS much more than the amount of MM. This effect was seen In many experiments with saliva from different subjects.

Addition of chlorhexidine had a clear effect on both HS and MM in the same order of magnitude as zinc acetate. The other antibacterials were effective, but much less so than chlorhexidine or zinc. However, when combinations of zinc acetate and the different antibacterials were tested, a clear further reduction in VSCs was observed, both for HS and MM. It can be seen that chlorhexidine was not better than the other antibacterials in these experiments.

An examination was conducted to investigate whether the effect of the combinations of zinc acetate and the individual antibacterial agents represented a synergistic effect. This was performed according to the method of Behrenbaum (J.lnf. Dis. 137:122–130, 1978). The fractional inhibitory concentrations (the FIC index) was calculated based on the amounts (AUC) of hydrogen sulfide and methyl mercaptan formed under different conditions. A low AUC thus indicates presence of a strong inhibitor. The FIC index was calculated from the following formula: (A+B)/A+(A+B)/B, where A+B represents the combinations of zinc and antibacterial agent, whereas A and B alone represent the individual agents.

If the FIC Index is below 1 (<1) a synergistic effect is established. If the index is like 1 (=1) an additional effect between A and B is seen, whereas an index above 1 (>1) indicates an antagonistic effect. The FIC index of the different combinations is seen in Table 1. All the different combinations had synergistic effect against both HS and MM, but the effect was far stronger against MM, presumably because zinc acetate had a weaker effect against MM (table 1),

TABLE 1

The table contains the AUC values (amounts of VSCs) from FIG. 1–8 and the FIC index* for the combinations of zinc and the individual antibacterial agents.

| FIG. | Agents tested | HS | FIC index | MM | FIC index |
|---|---|---|---|---|---|
| 1 | Control | >27 mill | | >41 mill | |
| 2 | Zinc Ac. 0.3% | 150 000 | | 4 mill | |
| 3 | CHX 0.025% | 443 000 | | 355 000 | |
| 4 | CPC 0.025% | 5.2 mill | | 6.89 mill | |
| 5 | Benzalk 0.025% | 1.4 mill | | 1.7 mill | |
| 6 | Zinc Ac 0.3% + CHX 0.025% | 82 000 | 0.73 | 34 000 | 0.1 |
| 7 | Zinc Ac 0.3% + Benzalk. 0.025% | 47 000 | 0.33 | 13 000 | 0.01 |
| 8 | Zinc Ac 0.3% + CPC 0.025% | 37 000 | 0.24 | 1 000 | 0.00 |

AUC - area under curve
Ac - acetate
CHX - chlorhexidine acetate
Benzalk. - benzalkonium chloride
CPC; cethylpyridinium chloride
*A FIC index below 1 (<1) indicates a synergistic effect
HS - hydrogen sulfide
MM - methylmercaptane

EXAMPLE 2

It has been shown that aqueous mouthrinses with 6 mM cysteine give an immediate, steep rise in VSC formation in the oral cavity. The effect can be used as a test system by observing the effect of a cysteine rinse when a prerinse with an inhibitor of oral VSC formation is performed (for instance with zinc solutions). This system is described in U.S. Pat. No. 5,833,955 of Kleinberg et al. (1998). By subsequent cysteine rinses each hour after for instance a zinc solution, it can be shown how long the inhibitor is effective. In the following it was shown that with 0.3% of zinc acetate and 0.025% of each of the antibacterial agents chlorhexidine and cetylpyridinium chloride was effective for more than 5 hours. The experimental design described is presumably severe, and its seems likely that under "normal" conditions where no cysteine is introduced in the mouth, the duration of the effect would be expected to last considerably longer than the present results indicate. A limitation of the model is that only hydrogen sulfide is formed by the test subjects upon cysteine rinses. This is clearly shown when the mouth air is analyzed by gas chromatography, as in the present study. If the frequently used Halimeter is employed for measurement, this limitation is not obvious because the Halimeter operates by chemical sensors which cannot differentiate between hydrogen sulfide and methyl mercaptan. The present experiments thus show the inhibiting effect of the inhibitors on hydrogen sulfide only. However, in combination with the experiments in Example 1 (which examined the effect of the combinations on methyl mercaptan as well) the present experiments are judged to provide valid data.

Figure 9:
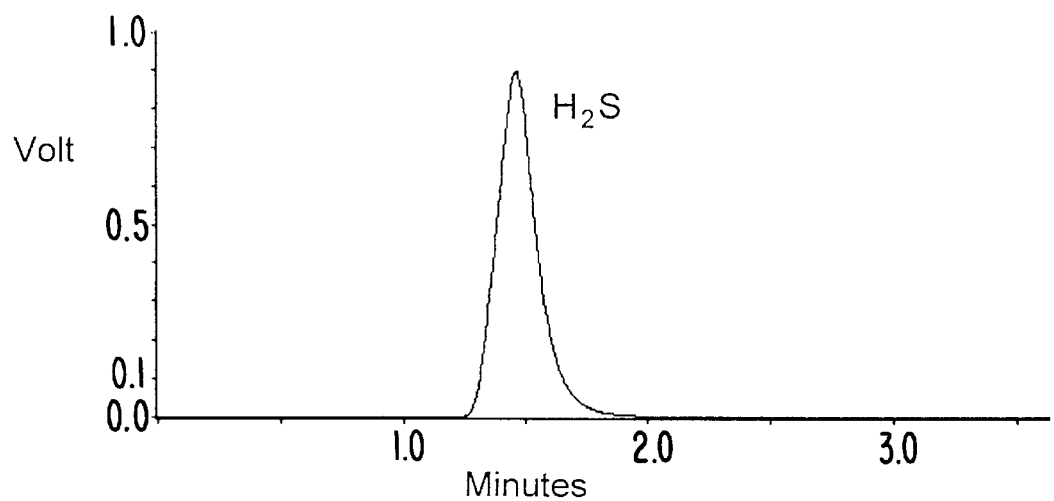
Figure 9A:
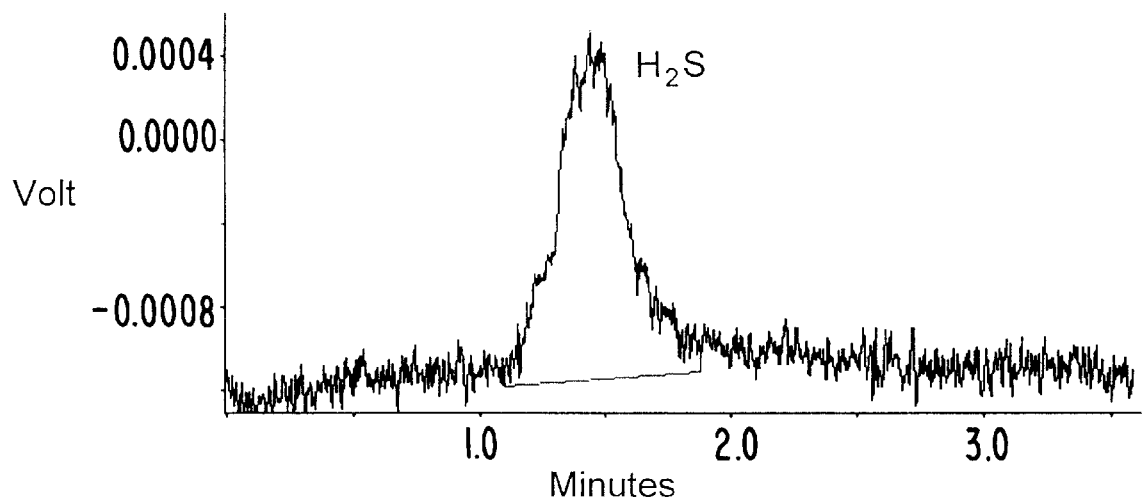
Figure 9B:
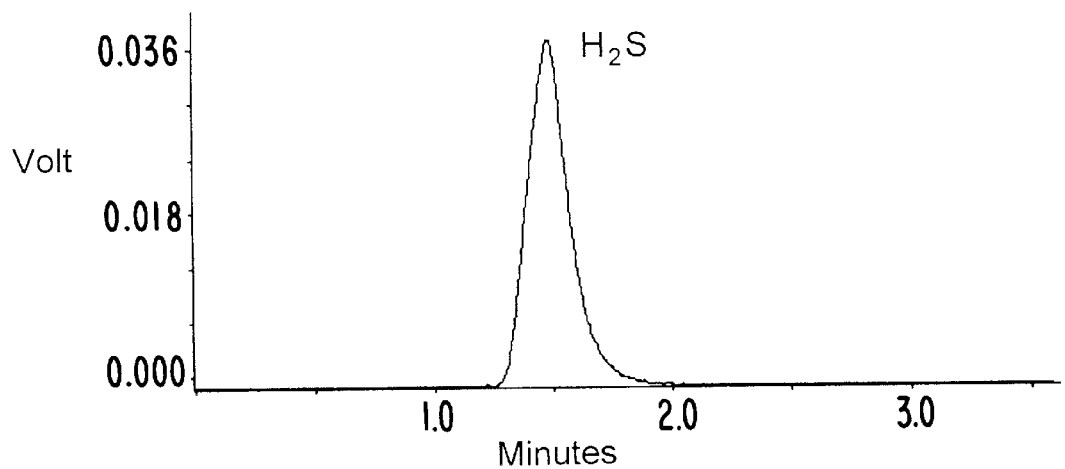
Figure 9C:
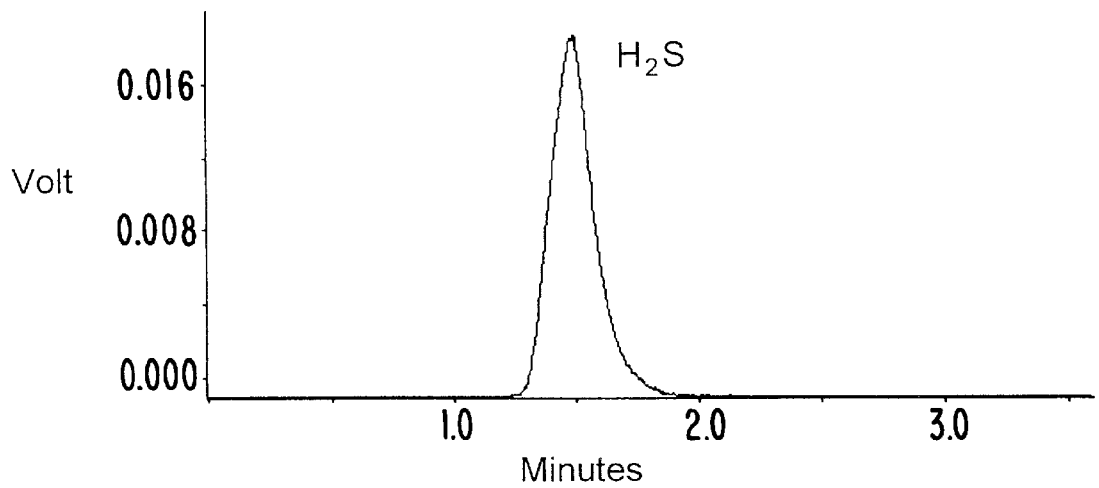
Figure 9D:
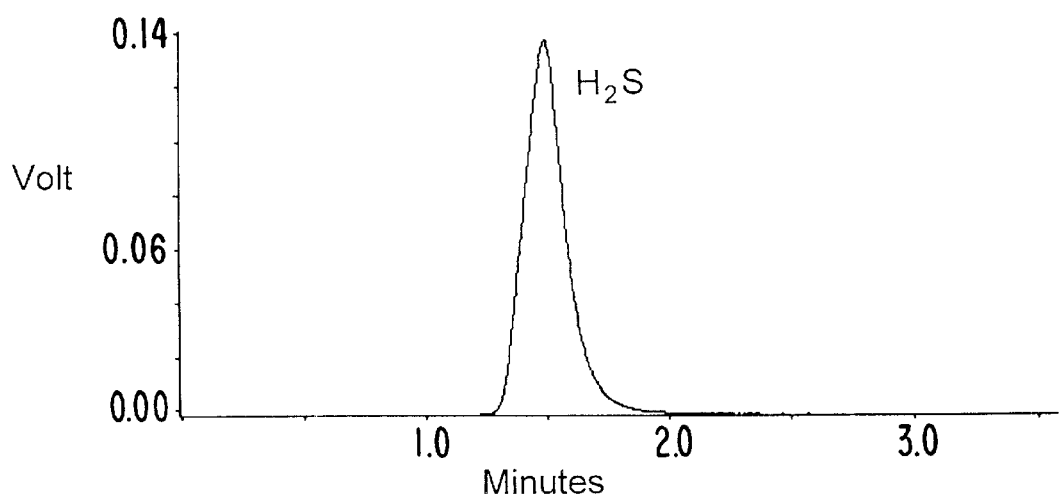
Figure 9E:
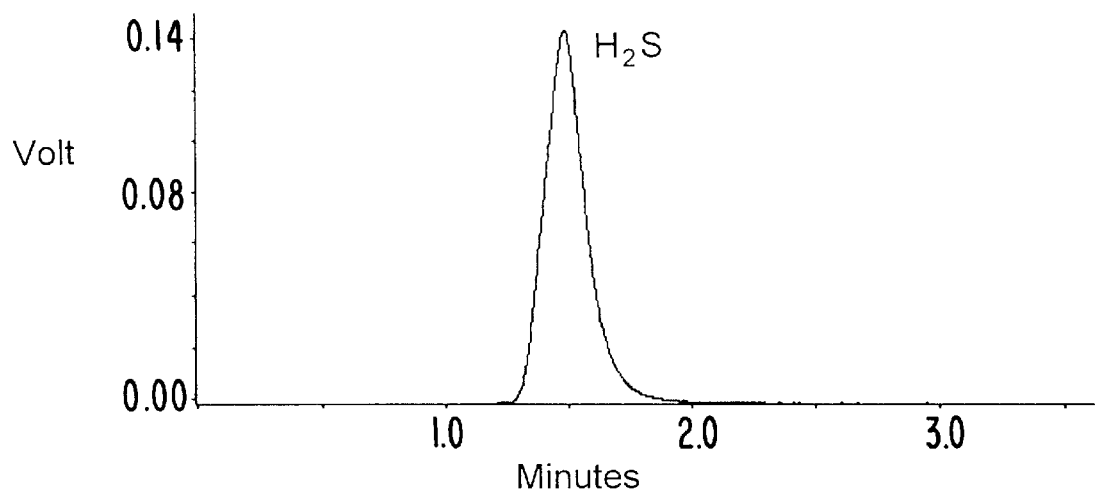

In the present experiments the test subject rinsed with 5 ml of a 6 mM cysteine solution and the VSC in the mouth air was examined after the mouth had been kept closed for 90 sec. The subject then rinsed with a VSC inhibitor (i.e. combinations of zinc acetate and the respective antibacterial agents). After one hour the subject again rinsed with cysteine. Any reduction in VSC (i.e. hydrogen sulfide) from the original values was assumed to be caused by the inhibitor. Cysteine rinses were performed each hour for 5 hours to establish the duration of the inhibiting effect. The results of these tests are shown in the chromatograms in FIGS. 9 and 10. FIG. 9 shows the normal hydrogen sulfide production by the test subject in the morning after a rinse with cysteine, which is 10 mill AUC. After a rinse with the combination of 0.3% zinc acetate and 0.025% of chlorhexidine acetate and a further rinse with cysteine one hour later the HS value was only 32,000 (FIG. 9*a*) after a further hour it was 500,000 (FIG. 9*b*), then 270,000 (FIG. 9*c*), 1.7 mill (FIG. 9*d*) and 1.7 mill (FIG. 9*e*). The combination thus reduced the hydrogen sulfide production in the mouth by cysteine with more than 80% five hours after a single rinse with the combination described above.

Figure 10:
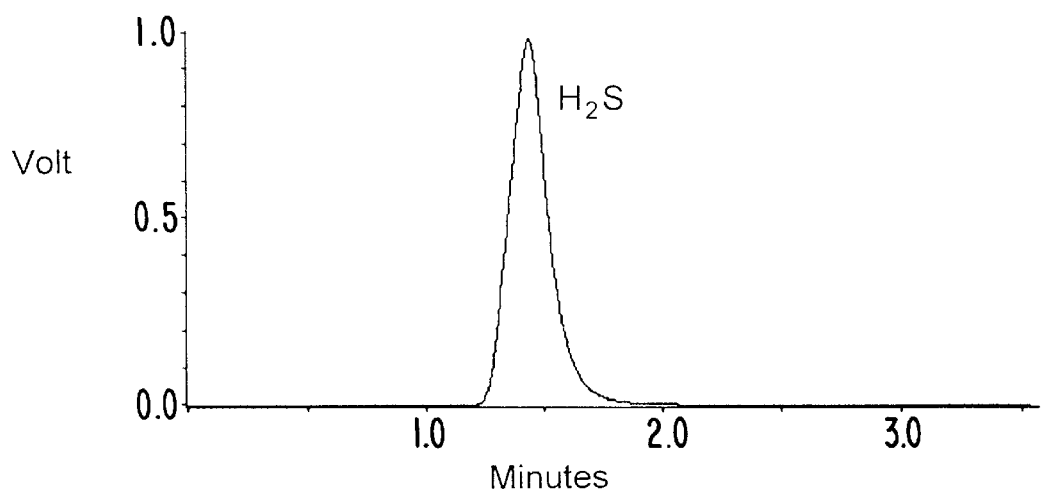
Figure 10A:
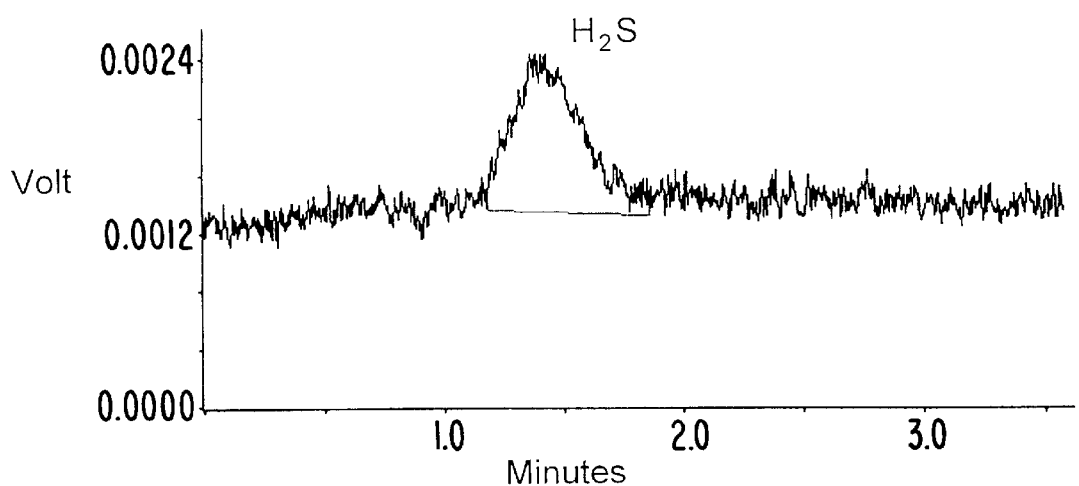
Figure 10B:
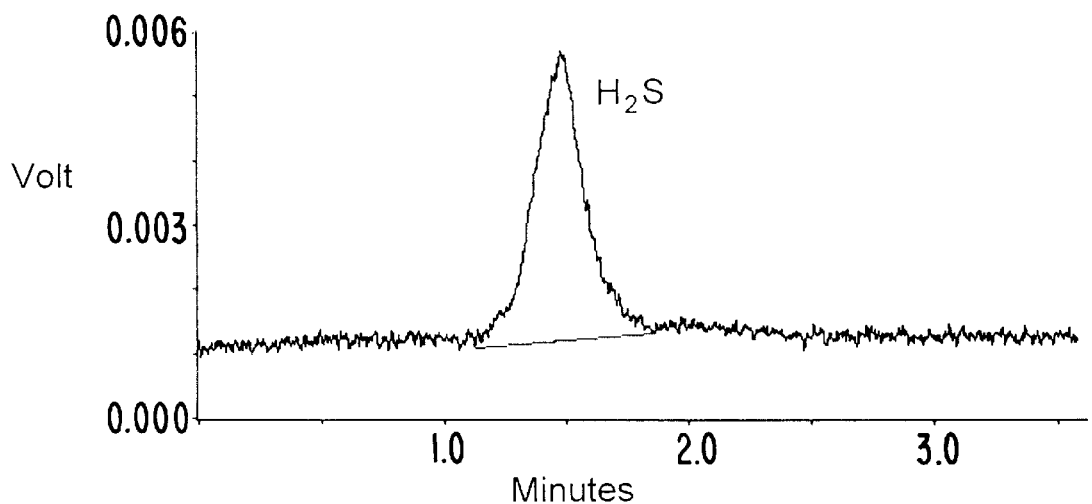
Figure 10C:
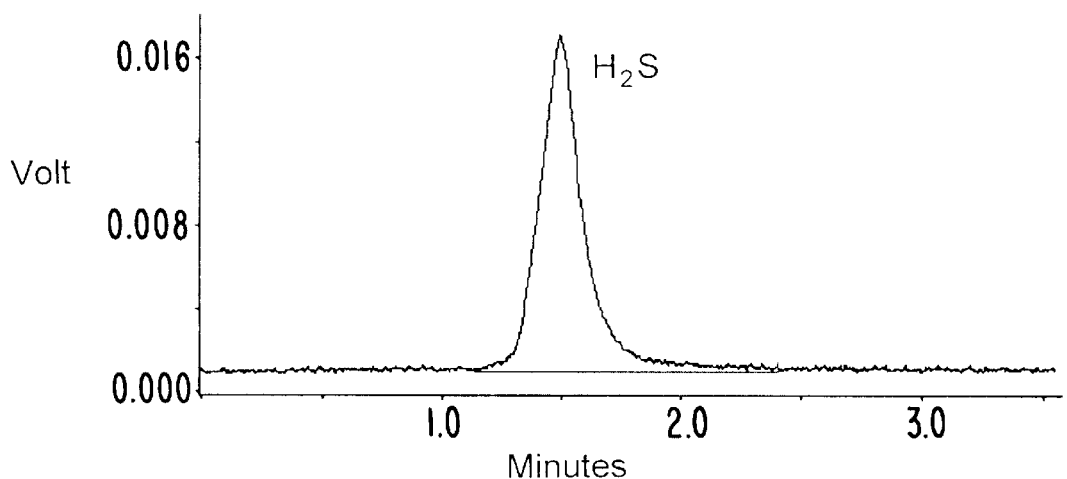
Figure 10D:
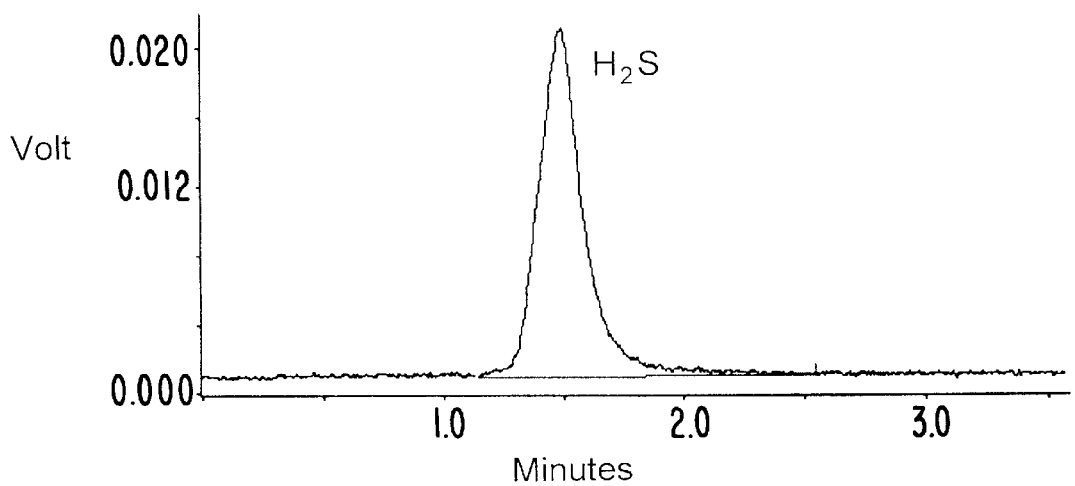
Figure 10E:
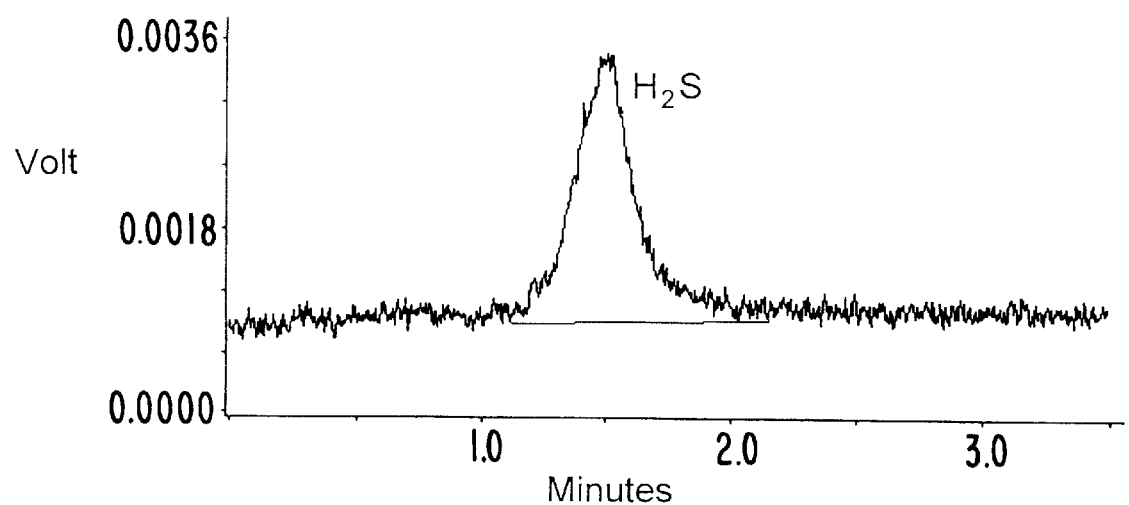

In a similar experiment with the combination of 0.3% zinc acetate and 0.025% cetylpyridinium chloride was tested. The normal value after the cysteine rinse was 11 mill AUC of hydrogen sulfide (FIG. 10). After a rinse with the combination and a cysteine rinse one hour later the HS value was as low as 22,000 (FIG. 10*a*). After two hours it was 67,000 (FIG. 10*b*), after three hours 315,000 (FIG. 10*c*), four hours 275,000 (FIG. 10*d*) and five hours 47,000 (FIG. 10*e*).

It can be concluded that the combinations of zinc acetate and the two tested antibacterials had a very strong and long lasting effect, and that chlorhexidine was not better than cetylpyridinium chloride in combination with zinc. It is probably safe to conclude that a mouthrinse of this type would inhibit oral malodor for eight hours or more under normal conditions.

It was furthermore evident from additional experiments with the individual agents in the present experimental model, that the anti-VSC effect of the individual antibacterial agents was markedly inferior to the effect of the combinations. Synergistic effects of combinations of zinc acetate and the antibacterial agents were thus demonstrated also in the vivo model, which included hydrogen sulfide only (results not shown).

What is claimed is:

1. An oral antihalitosis composition comprising an effective antihalitosis amount of a synergistic combination of 0.005–0.05% w/v of an antibacterial agent selected from bisguanides and quaternary ammonium compounds and 0.05–0.5% w/v of zinc acetate.

2. The oral antihalitosis composition according to claim 1, which comprises an effective antihalitosis amount of a synergistic combination of 0.01–0.025% w/v of the antibacterial agent and 0.1–0.3% w/v of zinc acetate.

3. The oral antihalitosis composition according to claim 1, wherein the antibacterial agent is chlorhexidine or a salt thereof.

4. The oral antihalitosis composition according to claim 2, wherein the antibacterial agent is chlorhexidine or a salt thereof.

5. The oral antihalitosis composition according to claim 1, wherein the antibacterial agent is a quaternary ammonium compound selected from cetyl pyridinium chloride and benzalkonium chloride.

6. The oral antihalitosis composition according to claim 2, wherein the antibacterial agent is a quaternary ammonium compound selected from cetyl pyridinium chloride and benzalkonium chloride.

* * * * *